United States Patent [19]

Bastioli et al.

[11] Patent Number: 5,462,980
[45] Date of Patent: Oct. 31, 1995

[54] FILM-FORMING, STARCHY, POLYMERIC COMPOSITION AND SHAPED ARTICLES, PARTICULARLY FILMS AND SHEETS, WHICH CAN BE PRODUCED FROM THE COMPOSITION AND HAVE A GOOD BARRIER EFFECT, AND A METHOD OF PRODUCING THE ARTICLES

[75] Inventors: Catia Bastioli, Novara; Vittorio Bellotti, Fontaneto d'Agogna; Gianfranco Del Tredici, Sesto Calende; Alessandro Montino, Robbio Lomellina; Roberto Ponti, Oleggio, all of Italy

[73] Assignee: Novamont S.p.A., Milan, Italy

[21] Appl. No.: 27,190

[22] Filed: Mar. 5, 1993

[30] Foreign Application Priority Data

Mar. 10, 1992 [IT] Italy ................... TO92A0199

[51] Int. Cl.⁶ .................. C08L 3/00; C08K 5/10; C08K 5/11
[52] U.S. Cl. .................. 524/47; 524/312; 524/377; 524/405
[58] Field of Search ............. 524/47, 312, 377, 524/405

[56] References Cited

U.S. PATENT DOCUMENTS

| | | | |
|---|---|---|---|
| 3,243,308 | 3/1966 | Barger et al. | 106/213 |
| 3,312,641 | 6/1963 | Young | 260/17.4 |
| 3,316,190 | 5/1962 | Suzumura et al. | 260/17.4 |
| 3,472,804 | 5/1966 | Nobile et al. | 260/17.3 |
| 3,652,542 | 3/1972 | Hiermstad et al. | 260/233.3 R |
| 3,867,324 | 2/1975 | Clendinning et al. | 260/23 H |
| 3,949,145 | 4/1976 | Otey et al. | 428/423 |
| 4,133,784 | 1/1979 | Otey et al. | 260/17.4 |
| 4,542,178 | 9/1985 | Zimmermann et al. | 524/388 |
| 4,673,438 | 6/1987 | Wittwer et al. | 106/126 |
| 4,863,655 | 9/1989 | Lacourse et al. | 264/53 |
| 4,900,361 | 2/1990 | Sachetto et al. | 106/213 |
| 5,035,930 | 7/1991 | Lacourse et al. | 428/35.6 |
| 5,043,196 | 8/1991 | Lacourse et al. | 428/35.6 |
| 5,095,054 | 3/1992 | Lay et al. | 524/47 |

FOREIGN PATENT DOCUMENTS

| | | |
|---|---|---|
| 0327505A2 | 1/1969 | European Pat. Off. |
| 0032802A1 | 1/1981 | European Pat. Off. |
| 0282451A2 | 3/1988 | European Pat. Off. |
| 0298920A2 | 7/1988 | European Pat. Off. |
| 0304401A2 | 8/1988 | European Pat. Off. |
| 0326517A1 | 1/1989 | European Pat. Off. |
| 0391853A2 | 3/1990 | European Pat. Off. |
| 0400532A1 | 6/1990 | European Pat. Off. |
| 0404723A2 | 6/1990 | European Pat. Off. |
| 0404727A2 | 6/1990 | European Pat. Off. |
| 0404728A2 | 6/1990 | European Pat. Off. |
| 0407350A2 | 7/1990 | European Pat. Off. |
| 0408502A2 | 7/1990 | European Pat. Off. |
| 0408503A2 | 7/1990 | European Pat. Off. |
| 0409781A2 | 7/1990 | European Pat. Off. |
| 0409782A2 | 7/1990 | European Pat. Off. |
| 0409783A2 | 7/1990 | European Pat. Off. |
| 0409788A2 | 7/1990 | European Pat. Off. |
| 0409789A2 | 7/1990 | European Pat. Off. |
| 400532 | 12/1990 | European Pat. Off. |
| 404723 | 12/1990 | European Pat. Off. |
| 554939 | 8/1993 | European Pat. Off. |
| 2190093 | 5/1987 | United Kingdom. |
| 2227245 | 7/1990 | United Kingdom. |
| WO90/10671 | 9/1990 | WIPO. |
| WO90/14938 | 12/1990 | WIPO. |
| WO-A-92/16584 | 10/1992 | WIPO. |

OTHER PUBLICATIONS

European Search Report dated Jan. 26, 1994.

Primary Examiner—Paul R. Michl
Assistant Examiner—LaVonda R. DeWitt
Attorney, Agent, or Firm—Bryan Cave

[57] ABSTRACT

The film-forming polymeric compositions described include a synthetic, thermoplastic polymer and a starchy material, with a high amylopectin content; they enable the production of films, sheets and the like having good liquid- and gas-barrier effects and improved mechanical properties.

18 Claims, 6 Drawing Sheets

FILM-FORMING, STARCHY, POLYMERIC COMPOSITION AND SHAPED ARTICLES, PARTICULARLY FILMS AND SHEETS, WHICH CAN BE PRODUCED FROM THE COMPOSITION AND HAVE A GOOD BARRIER EFFECT, AND A METHOD OF PRODUCING THE ARTICLES

The present invention relates to film-forming starchy polymeric compositions and shaped articles, particularly films, sheets and filaments, which can be produced from the compositions.

Native starches consist essentially of two basic polymers of which one is a linear polymer known as amylose and the other is a branched polymer known as amylopectin. By virtue of its characteristics as a linear polymer, amylose is a film-forming polymer. For this reason, in the technology relating to the production of films from starchy materials, the use of starches which have high amylose contents is usually required and, by virtue of their linear polymeric chains, these produce films having quite good mechanical properties.

In particular, the U.S. Pat. No. 3,243,308, which describes the production of self-supporting and flexible amylose films, requires the use of pure amylose or of an amylose material having an amylose content of at least 50% by weight. The amylose material is extruded in the presence of a quantity of water which is insufficient to dissolve it and, possibly, a plasticiser. The film emerging from the extrusion orifice is preferably stretched axially so as to achieve a considerable degree of orientation, the linear amylose molecules being oriented parallel to the extrusion axis.

The U.S. Pat. No. 3,312,641 describes the production of films by the casting or simple extrusion of compositions including starch with a high amylose content (greater than 50%) and polyvinyl alcohol, which acts as a plasticiser.

More recently, patent application WO90/14938 describes the production of films from starchy materials with high amylose contents by means of an extrusion process which includes a degassing step to remove the water content of the fused material before the film is formed.

Polymeric compositions suitable for transformation into films and including starch and synthetic thermoplastic polymers have recently been described in patent literature.

The technology relating to these products includes two alternatives, that is i) the production of compositions in which the starch is incorporated in the polymeric matrix as a filler and which are produced by mixing substantially anhydrous starch and synthetic polymers and ii) the production of compositions in which the starch and the synthetic polymer interact and which are produced by mixing at a temperature above the melting points of the starch and the polymer in the presence of a plasticiser such as water or high-boiling plasticisers (typically 5–40% of water and/or plasticiser, with reference to the starch and water system).

Figure 1:
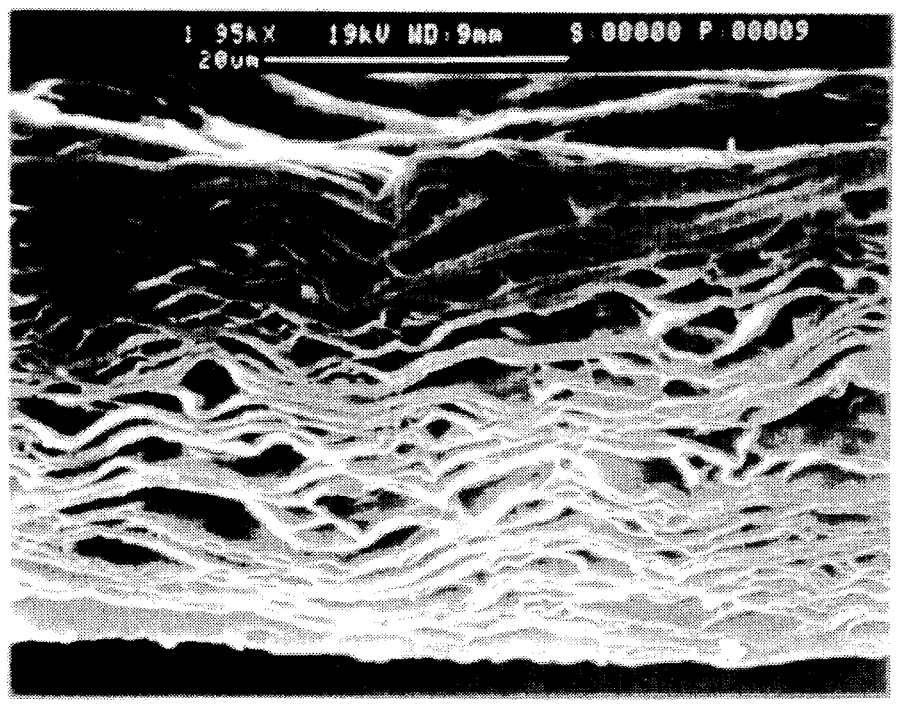
FIGS. 1–11 show the cross-sections of various polymeric film compositions produced from a starchy component and a synthetic thermoplastic polymeric component. The films were fractured in liquid nitrogen, brought to ambient temperature and buried for 3 days in fertile soil.

The present invention relates essentially to polymeric compositions produced by means of this second technology as described, for example, in patent applications WO90/10671, WO91/02025, WO91/2024 and EP-A-0 400 532, the descriptions of which are intended to be incorporated in the present description by reference.

In the production of film-forming polymeric blends produced by this technology, there is not generally any particular requirement as regards the nature of the starch used and inexpensive, native starches, particularly maize starch, are generally used, since the desired mechanical properties of the films are conferred essentially by the interaction between the starch and the synthetic polymer.

Surprisingly, it has now been discovered that, with the use of starchy materials with high amylopectin contents, it is possible to produce film-forming blends which, when transformed into films or sheets by conventional extrusion and blow-extrusion processes, have surprisingly improved liquid- and gas-barrier and mechanical properties in comparison with the films produced from conventional starches or from starches with high amylose contents.

A subject of the invention is therefore a polymeric composition which can be produced from a melt including a starchy material component and a synthetic, thermoplastic, polymeric component, characterised in that the starchy component is an amylopectin material.

It has surprisingly been found by microphotography carried out by a scanning electron microscope (SEM) on portions of sheets and films produced by the blow-extrusion of the polymeric compositions according to the invention that, in section, they have laminar structures formed by pluralities of laminar microphases of the synthetic polymer alternating with starchy phases in which the crystalline structure of the starch is no longer visible. Whilst it is not wished to be bound by a scientific explanation of these observations, it is thought that this laminar microstructure is produced during the stretching stage in the course of the blow-extrusion of the melt output from the extrusion orifice and that it is due essentially to the fact that, unlike amylose, amylopectin cannot form complexes with the polymeric component.

The laminar structure thus produced in fact considerably improves the liquid- and gas-barrier properties, presumably by virtue of the presence of a plurality of resistances to the passage of these fluids, arranged in series.

In particular, films have been produced having liquid water (moisture) permeability of considerably less than 400, and generally less than 200 gr. 30 microns/m$^2$.24 h at 23° C. and water vapour transmission rate of less than 400 gr 30 microns/m$^2$.24 h at 38° C. (Lyssi method).

The new films and sheets formed from blends of amylopectin material and synthetic thermoplastic polymers and having permeability and transmission properties which conform to the values indicated above which, up to now, have not been achieved, constitute a subject of the invention.

When films produced with the use of amylose starches or conventional starches are observed by SEM, on the other hand, they show a microstructure formed by microglobules constituted by an interpenetrated synthetic polymer and starch structure. It has been observed that the transition from the globular microstructure to the laminar structure takes place when the starchy component is formed by at least 78% of amylopectin and that the laminar structure becomes progressively more marked as the amylopectin content increases.

The term "amylopectin material" as used in the present description and in the claims, means a starchy material including at least 78% by weight of amylopectin. Materials including at least 80% of amylopectin, preferably at least 90%, and most preferably at least 94% by weight, are particularly advantageous. This material may be constituted by pure amylopectin, by starches with high amylopectin contents, such as "waxy" starches in particular which, typically, have amylopectin contents of the order of 95% by weight, and by mixtures thereof including mixtures of amylopectin, waxy starches and/or starches with lower amylopectin contents such as maize and potato starches.

In the compositions according to the invention, the amylopectin material preferably constitutes from 90 to 20% by weight, and most preferably from 80% to 30% by weight, with reference to the sum of the synthetic, thermoplastic, polymeric component and the starchy component.

The synthetic thermoplastic polymeric component is constituted by polymers and copolymers derived from ethylenically unsaturated monomers having repeating units with at least one polar functional group such as a hydroxy, alkoxy, carboxy, carboxyalkyl, alkylcarboxyl or acetal group. In particular, the invention envisages the use of polyvinyl alcohol and of copolymers of an olefin selected from ethylene, propylene, isobutene and styrene with acrylic acid, vinyl alcohol and/or vinyl acetate, such as ethylene-acrylic acid, ethylene-vinyl alcohol, ethylene-vinyl acetate copolymers and mixtures thereof. Particularly preferred are ethylene-vinyl alcohol copolymers with ethylene contents of from 10 to 44% by weight, produced by the hydrolysis of the corresponding ethylene-vinyl acetate with degrees of hydrolysis of between 50 and 100%.

Other preferred polymers include poly-epsilon-caprolactone and copolymers thereof, polyhydroxybutyrate/valerate and polymers or copolymers of lactic acid with glycolic acid or epsilon-caprolactone, chitin, chitosan and natural and synthetic thermoplastic gums and mixtures thereof with the polymers and copolymers mentioned above.

Compositions according to the invention which are particularly preferred are those in which the polymeric component is selected from:

poly-epsilon-caprolactone, mixtures of poly-epsilon-caprolactone and the polyethylene-vinyl alcohol mentioned above in ratios of from 1:4 to 4:1 by weight, and mixtures of polyethylene-vinyl acetate and poly-epsilon-caprolactone in ratios of from 1:4 to 4:1 by weight.

Another component generally used in the polymeric compositions according to the invention is a plasticiser of which the total quantity is between 1 and 50%, preferably between 5 and 25%, by weight with reference to the sum of the starchy component and the synthetic, polymeric component. The term plasticiser is intended to include water and aliphatic polyols and the acetate, ethoxylate and propoxylate derivatives thereof, particularly glycerine, ethylene or propylene glycol, ethylene or propylene diglycol, ethylene or propylene triglycol, polyethylene glycol, polypropylene glycol, 1,2-propandiol, 1,3-propandiol, 1,2-, 1,3-, 1,4-butandiol, 1,5-pentandiol, 1,6-, 1,5-hexandiol, 1,2,6-, 1,3,5-hexantriol, neopentyl glycol, trimethylol propane, pentaerythritol, sorbitol and the acetate, ethoxylate and propoxylate derivatives thereof, particularly sorbitol ethoxylate, glycerine ethoxylate, pentaerythritol ethoxylate, sorbitol acetate, pentaerythritol acetate and polyvinyl alcohol; a mixture of several plasticisers may be used.

According to another aspect of the invention, to advantage, the polymeric composition includes additives which can reduce the complexing capacity of the amylose and/or which can interact with the starch by hydrophilic interactions such as, for example, boric acid, borax, metaboric acid and aluminium hydroxide and alkali-metal salts, particularly chlorides.

Quantities of from 0.01 to 10%, preferably from 0.05 to 5% by weight, with reference to the weight of the starchy component, of these additives may be used.

It has been found that, with the use of these additives, the transition value of the amylopectin content of the starchy component at which the desired laminar structure can be produced is lower than and close to a value of approximately 70% by weight.

A further subject of the invention is therefore constituted by compositions and shaped articles (such as films, sheets and filaments) formed from a synthetic, thermoplastic, polymeric component and from a starchy component having an amylopectin content of more than 70% by weight and including a complexing agent such as that defined above.

Small quantities of hydrophobic polymers such as polyethylene, polypropylene and polystyrene may also be included in the formulations; in order to maintain good biodegradability characteristics, the quantities of these polymers used are preferably no greater than 5% by weight with reference to the total weight of the composition.

The compositions may also include agents which can destroy hydrogen bonds, such as urea, of which quantities of from 0.5 to 20% by weight, preferably from 2 to 7% by weight with reference to the total composition may be added to the mixture of the starchy and polymeric components, as well as cross-linking agents such as aldehydes, ketones and glyoxals, process coadjuvants, release agents and lubricants which are normally incorporated in compositions for moulding and extrusion, such as fatty acids, esters of fatty acids, higher alcohols, polyethylene waxes, antioxidants, opacifiers and stabilisers.

The polymeric blends according to the invention are prepared by the conventional methods described in the patent literature cited above. The mixing of the components is preferably effected in an extruder, although this may be carried out in any device which ensures temperature and shear-stress conditions suitable to render the amylopectin material and the polymeric fraction compatible from a rheological point of view. The preferred method of preparing the compositions according to the invention includes the steps of:

swelling the amylopectin material and the synthetic polymer by means of the plasticiser available and possibly the water present at a temperature of between 80° and 180°; this effect may be achieved, for example, during a first stage of the transportation of the components through an extruder for a period of time of the order of from 2 to 50 seconds, subjecting the mixture to shear-stress conditions corresponding to similar viscosity values of the polymeric and starchy components, degassing the mixture freely, under controlled pressure conditions or under vacuum, to produce a melt at a temperature of from 130° to 180° with a water content such that bubbles are not created at atmospheric pressure, for example, at the output of the extruder.

The melt may then be extruded directly in film form with the use of an extruder with a blowing, casting or spinning head or may be extruded and transformed into pellets for subsequent processing by conventional extrusion and blow-extrusion techniques.

The normal vertical stretch ratio typical for blow extrusion and the normal blowing ratio have been found to be suitable to form the desired laminar microstructure but, in order to prevent a high degree of orientation, a stretching ratio of between 1 and 5 and a blowing ratio of between 1.2 and 7 are preferred.

The production of this structure greatly modifies not only barrier properties but also mechanical properties such as, in particular, extensibility and breaking load and, above all, tear strength.

A further subject of the invention is therefore a method of producing films, sheets, fibres, filaments and the like which, in cross-section, have a substantially laminar structure, comprising the extrusion of a melt including a synthetic, thermoplastic, polymeric component and an amylopectin material as defined above, in which the melt output from the extruder is subjected to axial stretching.

EXAMPLE 1

38 parts of waxy Snowflake starch 04201 (registered trade mark) (12% by weight of water, amylopectin content approximately 95% by weight), 38 parts of ethylene-vinyl alcohol with an ethylene content of 44% in moles and a degree of hydrolysis of the acetate groups of 99.5%, 5 parts of urea, 12 parts of sorbitol mono-ethoxylate, 4 parts of glycerine and 3 parts of water were introduced into an OMC extruder with a diameter of 20 mm, a screw length-diameter ratio L/D of 30 and a screw with a compression ratio of 1:3.

The process was carried out with the use of the following temperature profile: 90°–180°–150°–140° C. and a degassing zone within the extruder.

The extruded and granulated product had a water content of 3.5% by weight and was filmed with the use of a 19 mm HAAKE extruder with an L/D of 28 and a HAAKE filming head for cable sheathing. The diameter of the die was 25 mm with a 0.5 mm wide hole and an L/D of 10. The stretching and blowing ratios used were 3.2 and 3.5, respectively.

The film produced was fractured in liquid nitrogen and then brought to ambient temperature and buried for 3 days in fertile soil. FIG. 1 shows the cross-section of the treated film observed by a scanning electron microscope. A layered structure with layers less than 1 micron thick was displayed.

EXAMPLE 2 (COMPARATIVE)

Figure 2:
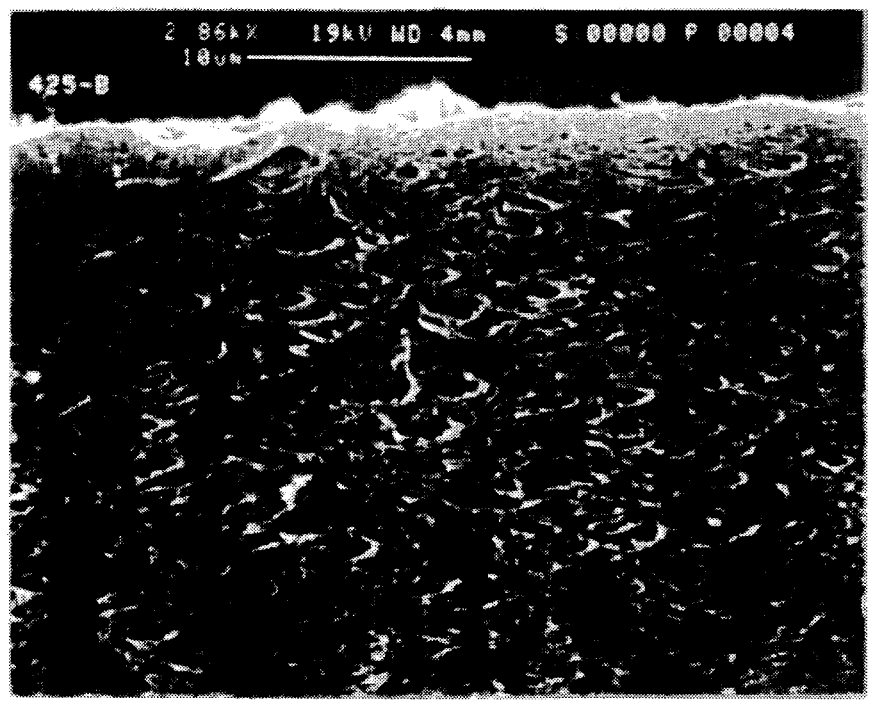
Figure 3:
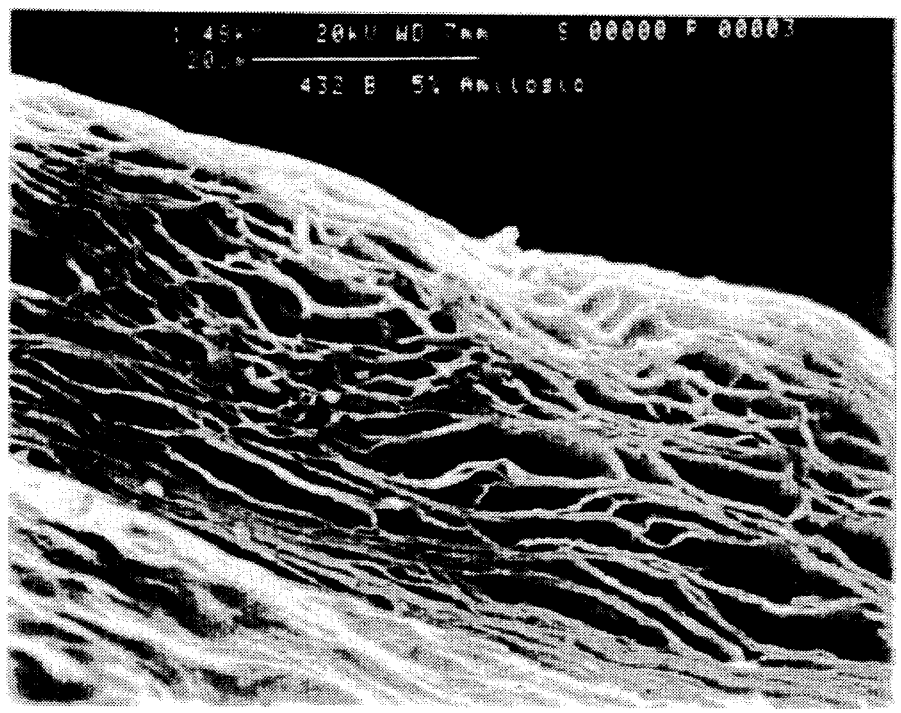
Figure 4:
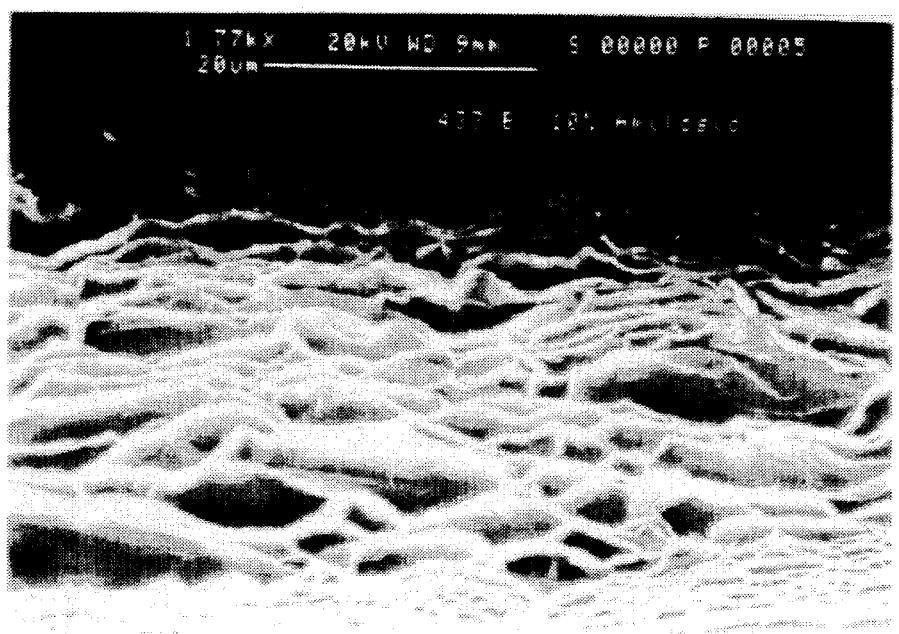
Figure 5:
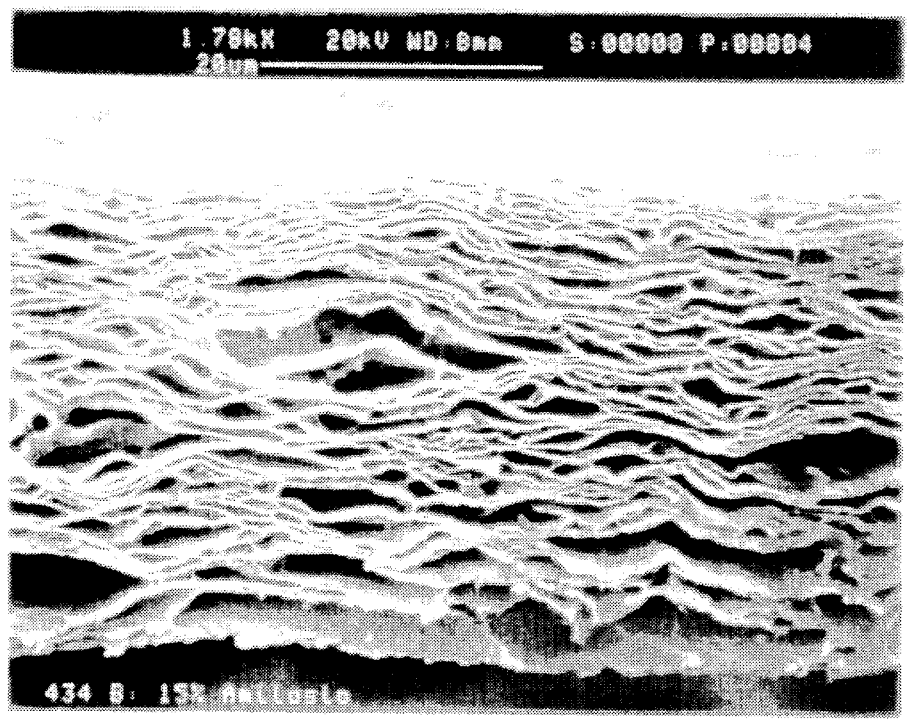
Figure 6:
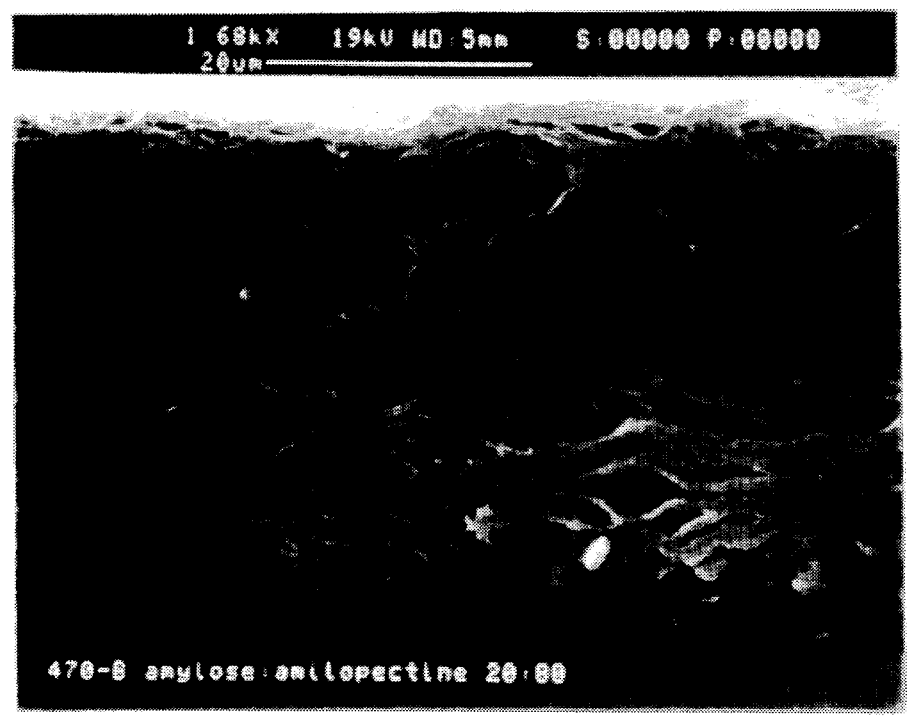
Figure 7:
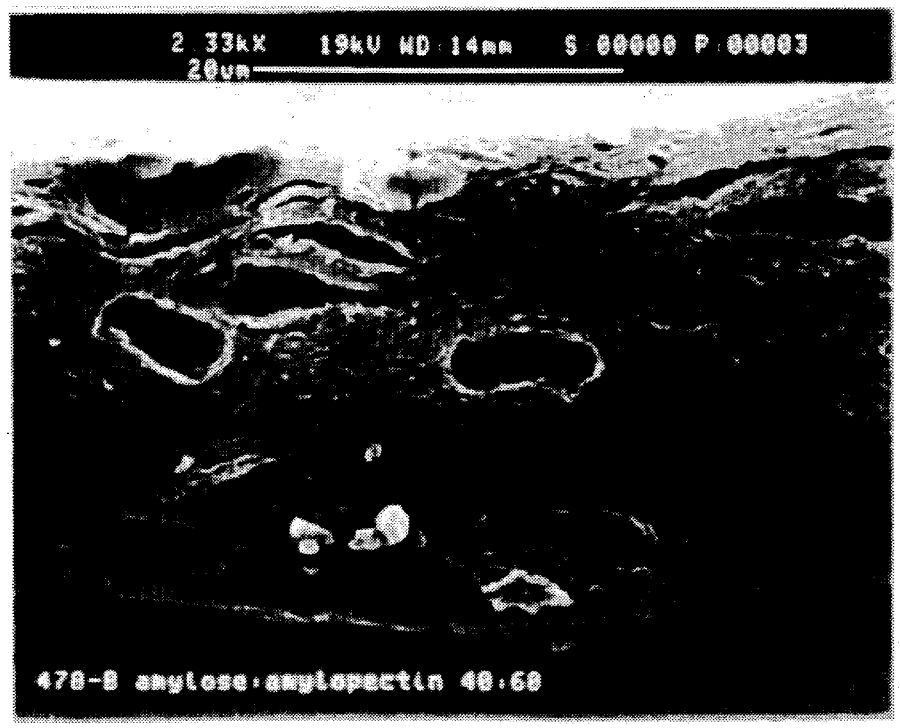

The method of Example 1 was used but the waxy starch was replaced by normal GLOBE E3401 (registered trade mark) maize starch (12% by weight of water, amylopectin content approximately 70% by weight). The electron micrograph of FIG. 2 shows a non-layered structure.

Table 1 gives the water vapour transmission rate value (Lyssi method, 38° C., 90% relative humidity) and the moisture permeability value (20° C., part not in contact with the water, with relative humidity of less than 10%) of the film produced under the conditions described above and in comparison with the film of Example 1.

EXAMPLES 2A AND 2B (COMPARATIVE)

The method of Example 2 was used with different stretching and blowing ratios.

Non-layered structures of the type shown in FIG. 2 were produced; the water vapour transmission rate and moisture permeability values are given in Table 1.

EXAMPLES 3–7

The method of Example 1 was used with the waxy Snowflake 4201 (registered trade mark) starch replaced by a mixture of amylopectin and Eurylon F1672 (registered trade mark, Roquette Freres) amylose in the percentages given in Table 2. The scanning electron micrographs of the portions of film after treatment for 3 days in fertile soil are given in FIGS. 3–7; as the amylose content increases, there is a transition from a completely layered structure to a compact structure.

EXAMPLES 8–9

Figure 8:
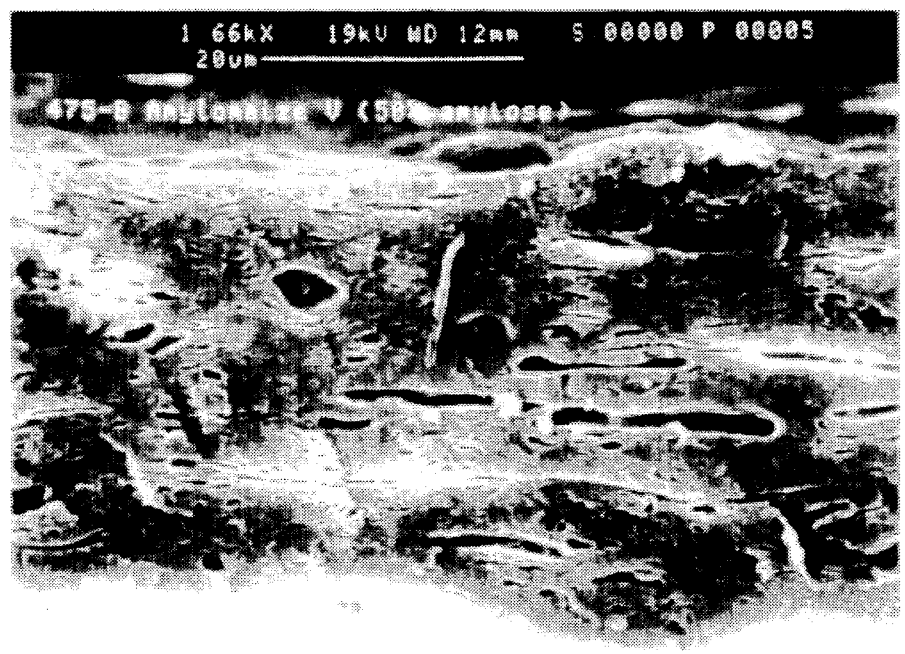
Figure 9:
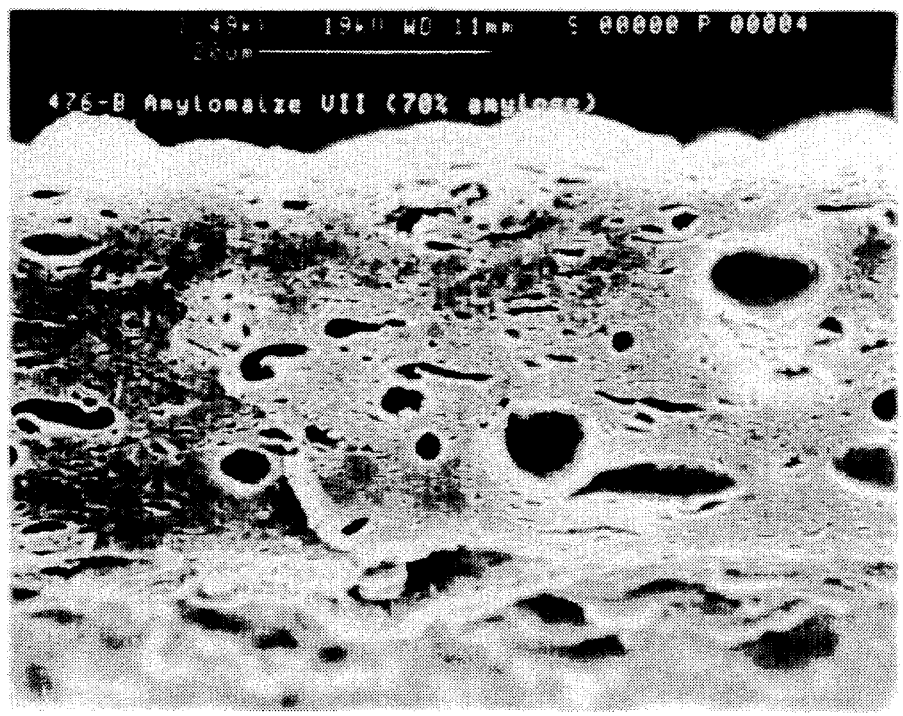

The method of Example 1 was used and the waxy starch was replaced by amylomaize V and VII starch (Cerestar). In neither case was any layered structure observed (see FIGS. 8 and 9).

EXAMPLE 10

55 parts of waxy starch such as that used in Example 1, 20 parts of ethylene-vinyl alcohol with an ethylene content of 44% in moles and a degree of hydrolysis of the acetate groups of 98.5%, 5 parts of urea, 13 parts of sorbitol mono-ethoxylate, 4 parts of glycerine and 3.5 parts of water were extruded as in Example 1. The film, which was produced under the conditions described in Example 1, gave a layered structure of the type shown in FIG. 1.

EXAMPLE 11

38 parts of the waxy starch used in Example 1, 21 parts of ethylene-vinyl alcohol copolymer with an ethylene content of 44% in moles and a degree of hydrolysis of the acetate groups of 99.5%, 18 parts of ethylene-acrylic acid copolymer, 5 parts of urea, 10 parts of sorbitol mono-ethoxylate, 5 parts of glycerine and 3 parts of water were extruded as in Example 1. The film, which was produced under the conditions described in Example 1, gave a layered structure of the type shown in FIG. 1.

EXAMPLE 12

Figure 10:
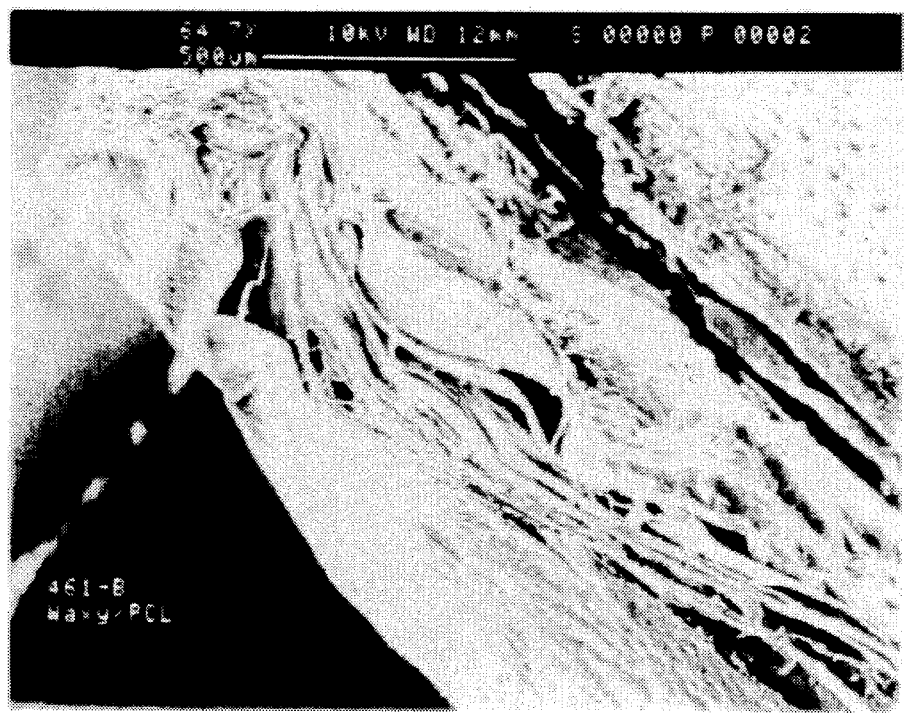

38 parts of the waxy starch used in Example 1, 21 parts of poly-epsilon-caprolactone P787 (Union Carbide), 7 parts of urea, 10 parts of sorbitol mono-ethoxylate, 3 parts of glycerine and 3 parts of water were extruded as in Example 1. The film, which was produced under the conditions of Example 1, gave a layered structure of the type shown in FIG. 10.

EXAMPLE 13

Example 12 was repeated but with the use of 55 parts of waxy starch and 21 parts of poly-epsilon-caprolactone P787 (Union Carbide) and with the concentrations of the other components unchanged. In this case, a structure similar to that shown in FIG. 10 was again obtained.

EXAMPLE 14

Figure 11:
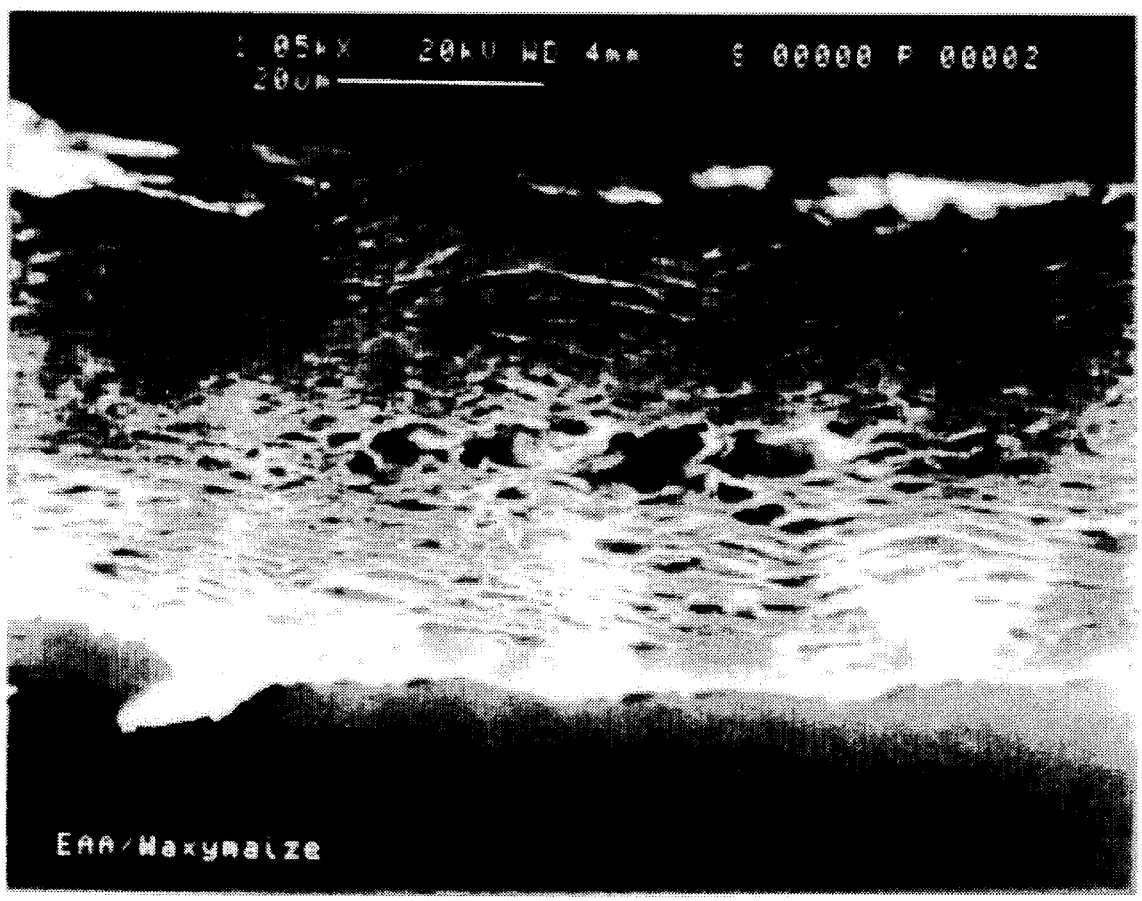

38 parts of waxy starch as used in Example 1, 38 parts of ethylene-acrylic acid copolymer with 20% of acrylic acid, 7 parts of urea, 10 parts of sorbitol mono-ethoxylate, 3 parts of glycerine and 3 parts of water were extruded as in Example 1. The film, which was produced under the conditions of Example 1, gave a layered structure of the type shown in FIG. 11.

EXAMPLE 15

The method of Example 14 was repeated but with the use of 55 parts of waxy starch and, correspondingly, 17 parts of ethylene-acrylic acid copolymer, with the concentrations of the other components unchanged. In this case, a layered structure of the type shown in FIG. 11 was again obtained.

EXAMPLE 16

38 parts of waxy starch as used in Example 1, 21 parts of ethylene-vinyl alcohol copolymer with an ethylene content of 44% in moles and a degree of hydrolysis of the acetate groups of 99.5%, 18 parts of poly-epsilon-caprolactone P787 (Union Carbide), 5 parts of urea, 10 parts of sorbitol mono-ethoxylate, 5 parts of glycerine and 3 parts of water were extruded as in Example 1. The film, which was produced under the conditions of Example 1, gave a structure exactly the same as that shown in FIG. 11.

EXAMPLE 17

38 parts of waxy starch as used in Example 1, 38 parts of ethylene-vinyl alcohol copolymer with an ethylene content of 44% in moles and a degree of hydrolysis of the acetate groups of 99.5%, 5 parts of urea, 0.3 parts of Armide E, 12 parts of sorbitol mono-ethoxylate, 3.7 parts of glycerine and 3 parts of water were supplied to an OMC 58 mm extruder with two screws and an L/D of 36.

The following working conditions were used:

screw speed (rpm): 170 degassing pressure (bars): 0.9 degassing position: 8th block (scheme 1)

heating profile:

1st region: cold

2nd region: 90° C.

3rd region: 140° C.

4th–7th regions: 180° C.

8th region: 175° C.

9th region: 165° C.

head: 145° C.—melt temperature: 145° C.

head pressure: 27 bars absorption (A): 67–69

The extruded rods were cooled in a water bath and granulated and were then supplied to a 40 mm Ghioldi bubble filming machine with an L/D of 30. The water content of the granules was 3.5%.

The screw used for the filming had a uniform profile with a compression ratio of 1:2.8.

The main characteristics of the filming head are summarised below:

spiral shape die diameter: 100 mm hole: 0.5 mm

L/d ratio: 10

The conditions used at the filming stage were as follows:

screw speed: 65 rpm extruder heating profile: 135°—135°–140°—140° C. (melt temperature: 152° C.)

neck heating profile: 140°—140° C. (melt temperature: 150° C.)

head heating profile: 135°—135° C. (melt temperature: 140° C.)

neck pressure: 274 bars die pressure: 73 bars stretching ratio: 3 blowing ratio: 3

Table 3 gives the mechanical characteristics under tension and upon tearing. Table 1 gives the moisture permeability and water vapour transmission rate values. The laminar structure was similar to that shown in FIG. 1.

EXAMPLE 18

37.5 parts of waxy starch such as that used in Example 1, 27 parts of ethylene-vinyl alcohol copolymer with an ethylene content of 44% in moles and a degree of hydrolysis of the acetate groups of 99.5%, 13% of plasticised polyvinyl alcohol (77% PVOH, 18% glycerine, 5% water) with a degree of hydrolysis of 85% and a molecular weight of 70,000, 5 parts of urea, 0.3 parts of Armide E, 10 parts of sorbitol mono-ethoxylate, 3.7 parts of glycerine and 3 of water were extruded as described in Example 17. The granules produced had a water content of 2.8%. Table 3 gives the mechanical characteristics under tension and upon tearing. The laminar structure was similar to that shown in FIG. 1.

EXAMPLE 19

37.5 parts of waxy starch such as that used in Example 1, 32.5 parts of ethylene-vinyl alcohol copolymer with an ethylene content of 44% in moles and a degree of hydrolysis of the acetate groups of 99.5%, 6 parts of plasticised polyvinyl alcohol (77% PVOH, 18% glycerine, 5% water) with a degree of hydrolysis of 85% and a molecular weight of 70,000, 5 parts of urea, 0.2 parts of Armide E, 13 parts of sorbitol mono-ethoxylate, 3.2 parts of glycerine, and 2.5 parts of water were extruded as described in Example 17. The granules produced had a water content of 2.4%. Table 3 gives the mechanical characteristics relating to tensile strength and tearing strength. The laminar structure was similar to that shown in FIG. 1.

EXAMPLE 20

38 parts of waxy starch as used in Example 1, 38 parts of ethylene-vinyl alcohol copolymer as used in Example 19, 5 parts of urea, 0.3 parts of Armide E, 0.2 parts of boric acid, 12 parts of sorbitol mono-ethoxylate, 3.5 parts of glycerine and 3 parts of water were supplied to an extruder according to the method of Example 17 with the sole difference that the degassing region was left open.

Table 3 gives the mechanical tensile and tearing strength properties. The laminar structure was similar to that shown in FIG. 1.

EXAMPLES 21–22

The granules of the product produced in Example 17 were blended with poly-epsilon-caprolactone P787 (Union Carbide) in proportions of 50/50 and 60/40, respectively directly during the filming stage in Ghioldi equipment. Table 3 gives the mechanical characteristics under tension and upon tearing. Table 1 gives the water-permeability.

The product produced was orientable by stretching also giving rise to fibrillation phenomena.

EXAMPLE 23

The method of Example 17 was used, but the waxy starch was replaced by normal Global 3401 (Cerestar) maize starch. The structure was of the type shown in FIG. 2.

Table 3 gives the mechanical properties under tension and the behaviour upon tearing.

TABLE 1

| Example | Stretch ratio | Blowing ratio | Water vapour transmission rate (gr 30 microns/ $m^2 \cdot 24$ h) | Moisture permeability (gr 30 microns/ $m^2 \cdot 24$ h) |
| --- | --- | --- | --- | --- |
| 1 | 3.2 | 3.5 | 96 | 334 |
| 2 | 3.2 | 3.5 | 870 | 820 |
| 2A | 3 | 3 | 875 | 828 |
| 2B | 4 | 3 | 785 | 722 |
| 17 | 3 | 3 | 290 | 120 |
| 18 | 3 | 3 | 170 | 80 |

TABLE 2

| Example | Amylopectin (%) | Amylose Eurylon F1672 (%) |
| --- | --- | --- |
| 3 | 95 | 5 |
| 4 | 90 | 10 |
| 5 | 85 | 15 |
| 6 | 80 | 20 |
| 7 | 60 | 40 |

TABLE 3

| Example | $\sigma y$ (MPa) | $\epsilon y$ (%) | $\sigma b$ (MPa) | $\epsilon b$ (%) | E (MPa) | En (Kj/m2) | Tearing Longitud. I N/mm | Tearing Longitud. P N/mm | Tearing trasver. I N/mm | Tearing trasver. P N/mm |
| --- | --- | --- | --- | --- | --- | --- | --- | --- | --- | --- |
| 17 | 7.6 | 6.1 | 23 | 428 | 272 | 3270 | 4.1 | 4.6 | 51.4 | 52 |
| 18 | 8.2 | 57 | 20.2 | 381 | 180 | 2455 | — | — | — | — |
| 19 | 7 | 7 | 22.7 | 354 | 241 | 2781 | 3.7 | 4.4 | 37.4 | 35.1 |
| 20 | 7.2 | 14.6 | 20.8 | 484 | 283 | 3190 | — | — | — | — |
| 21 | 11.7 | 6.6 | 29.4 | 765 | 425 | 6764 | 43 | 43 | 76 | 76 |
| 22 | 11.6 | 10.1 | 33.2 | 864 | 365 | 8441 | 47 | 47 | 90 | 90 |
| 23 | 8.5 | 15.2 | 19.3 | 338 | 195 | 2040 | 4 | 4.2 | 5.1 | 5.3 | sigma y = tensile strength at yeld point
epsilon y = elongation at yeld point
sigma b = tensile strength at break
epsilon b = elongation at break
En = breaking energy
E = Young's modulus
I = tear strength (initiation)
P = tear strength (propagation)

We claim:

1. A polymeric composition which can be produced from a melt comprising:
   i) a starchy material component;
   ii) a synthetic, thermoplastic, polymeric component; and
   iii) a quantity of from 2 to 7% by weight of urea, with reference to the weight of the total composition,
   wherein the starchy material includes at least 78% by weight of amylopectin.

2. A polymeric composition according to claim 1, in which the starchy material comprises at least 80% by weight of amylopectin.

3. A polymeric composition according to claim 1, wherein the weight ratio of the starchy material component, comprising at least 78% by weight of amylopectin, to the synthetic, thermoplastic polymeric component, ranges from about 1:4 to 9:1.

4. A polymeric composition according to claim 1, in which the synthetic, thermoplastic, polymeric component comprises a polymer derived from at least one ethylenically unsaturated monomer, the polymer having repeating units having at least one polar functional group selected from the group consisting of hydroxy, alkoxy, carboxy, carboxyalkyl, alkylcarboxyl and acetal groups.

5. A polymeric composition according to claim 4, in which the synthetic, thermoplastic, polymeric component comprises:
   i) polyvinyl alcohols,
   (ii) a polymer or a copolymer of an olefin selected from the group consisting of ethylene, propylene, isobutene and styrene with acrylic acid, vinyl alcohol or vinyl acetate or mixtures of these polymers and copolymers of an olefin, or
   (iii) a mixture of (i) and (ii).

6. A polymeric composition according to claim 5, in which the synthetic, thermoplastic, polymeric component comprises a polymer selected from the group consisting of polyvinyl alcohol, ethylene-acrylic acid, ethylene-vinyl alcohol, ethylene-vinyl acetate and mixtures thereof.

7. A polymeric composition according to claim 3, in which the synthetic, thermoplastic, polymeric component comprises a polymer selected from the group consisting of poly-epsilon-caprolactone and copolymers thereof, polyhydroxybutyrate/valerate, polymers of lactic acid and copolymers thereof with glycolic acid or epsilon-caprolactone, chitin, chitosan, natural and synthetic thermoplastic gums and mixtures thereof.

8. A polymeric composition comprising:
   i) a starchy material component, including at least 78% by weight of amylopectin; and
   ii) a synthetic, thermoplastic, polymeric component;
   wherein said polymeric composition comprises from 20 to 90% by weight of amylopectin material with reference to the sum of the synthetic, thermoplastic, polymeric component and the starchy component, and wherein the synthetic, thermoplastic, polymeric component comprises a mixture of poly-epsilon-caprolactone and polyethylene-vinyl alcohol in a ratio of from 1:4 to 4:1 by weight.

9. A polymeric composition comprising:
   i) a starchy material component, including at least 78% by weight of amylopectin; and
   ii) a synthetic, thermoplastic, polymeric component;
   wherein said polymeric composition comprises from 20 to 90% by weight of amylopectin material with reference to the sum of the synthetic, thermoplastic, polymeric component and the starchy component, and
   wherein the synthetic, thermoplastic, polymeric component includes a mixture of polyethylene-vinyl acetate and poly-epsilon-caprolactone in a ratio of from 1:4 to 4:1 by weight.

10. A polymeric composition according to claim 1, further comprising from 1 to 50% by weight, with reference to the sum of the synthetic, thermoplastic, polymeric component and the starchy component, of a plasticiser selected from the group consisting of glycerine, ethylene glycol, propylene glycol, ethylene diglycol, propylene diglycol, ethylene triglycol, propylene triglycol, polyethylene glycol, polypropylene glycol, 1,2-propandiol, 1,3-propandiol, 1,2-, 1,3-, 1,4-butandiol, 1,5-pentandiol, 1,6-, 1,5-hexandiol, 1,2,6-, 1,3,5-hexantriol, neopentyl glycol, trimethylol propane, sorbitol, pentaerythritol, glycerine ethoxylate, sorbitol ethoxylate, pentaerythritol ethoxylate, sorbitol acetate, pentaerythritol acetate and mixtures thereof.

11. A polymeric composition according to claim 1, further comprising a quantity of from 0.01 to 10% by weight, with reference to the weight of the amylopectin material, of a hydrophilic agent which can interact with the starch by means of hydrophilic interactions.

12. A polymeric composition according to claim 1, further comprising a quantity of from 0.01 to 10% by weight, with reference to the weight of the amylopectin material, of an hydrophilic agent which can interact with the starch by means of hydrophilic interactions, wherein said agent is selected from the group consisting of boric acid, aluminum hydroxide, borax and metaboric acid.

13. A composition according to claim 1, further processed to provide shaped articles.

14. A film having a water permeability at 23° C. of less than 400 gr.30 microns/$m^2$.24 hr, which can be prepared by the extrusion or blow extrusion of a polymeric composition including a starchy polymeric component and a synthetic thermoplastic polymeric component, in which the starchy polymeric component includes at least 78% by weight of amylopectin.

15. A film according to claim 14, having water vapour transmission rate (38° C.) of less than 400 gr 30 microns/$m^2$.24 h.

16. A polymeric composition according to claim 2, wherein the starchy material comprises at least 90% by weight of the amylopectin.

17. A polymeric composition according to claim 1, further processed with an additional step of molding, shaping, or extruding to provide films, sheets and filaments.

18. A method of producing films, sheets, fibers and filaments by the extrusion of a melt including a synthetic, thermoplastic, polymeric component and an amylopectin component, in which the melt output from the extruder is subjected to axial stretching.

* * * * *